United States Patent [19]

Evans et al.

[11] Patent Number: 4,943,582

[45] Date of Patent: Jul. 24, 1990

[54] ACTIVE COMPOUNDS

[75] Inventors: John M. Evans; Geoffrey Stemp; Frederick Cassidy, all of Harlow, England

[73] Assignee: Beecham Group p.l.c., England

[21] Appl. No.: 45,626

[22] Filed: May 1, 1987

[30] Foreign Application Priority Data

May 3, 1986 [GB] United Kingdom ............... 8610911
Oct. 3, 1986 [GB] United Kingdom ............... 8623768

[51] Int. Cl.$^5$ .................. A61K 31/40; A61K 31/35; C07D 405/04
[52] U.S. Cl. .................. 514/320; 514/409; 514/422; 546/196; 548/407; 548/525; 549/399; 549/404; 549/407
[58] Field of Search .............. 548/525; 546/196; 514/422, 320, 409, 548, 407

[56] References Cited

U.S. PATENT DOCUMENTS

| | | | |
|---|---|---|---|
| 4,251,537 | 2/1981 | Evans et al. | 544/62 X |
| 4,363,811 | 12/1982 | Evans et al. | 546/196 X |
| 4,366,163 | 12/1982 | Evans et al. | 546/196 X |
| 4,446,113 | 5/1984 | Evans et al. | 548/525 X |
| 4,481,214 | 11/1984 | Evans | 549/399 X |
| 4,510,152 | 4/1985 | Faruk | 546/196 X |
| 4,571,406 | 2/1986 | Evans et al. | 514/456 |
| 4,575,511 | 3/1986 | Evans et al. | 514/456 |
| 4,610,992 | 9/1986 | Evans et al. | 546/196 X |
| 4,629,734 | 12/1986 | Ashwood | 548/525 X |
| 4,687,779 | 8/1987 | Evans | 546/196 X |
| 4,738,963 | 4/1988 | Hamilton et al. | 514/422 X |
| 4,772,603 | 9/1988 | Evans | 514/422 X |
| 4,786,639 | 11/1988 | Evans | 514/422 X |

FOREIGN PATENT DOCUMENTS

| | | |
|---|---|---|
| 0076075 | 4/1983 | European Pat. Off. . |
| 0095316 | 11/1983 | European Pat. Off. . |
| 0218373 | 4/1987 | European Pat. Off. . |
| 183551 | 9/1978 | Netherlands . |
| 201984 | 4/1986 | New Zealand . |
| 213468 | 4/1986 | New Zealand . |
| 204297 | 10/1986 | New Zealand . |
| 208170 | 7/1987 | New Zealand . |
| 208169 | 8/1987 | New Zealand . |

OTHER PUBLICATIONS

Evans, et al.; Journal of Medicinal Chemistry, (1983), vol. 26, pp. 1582–1589.
Evans, et al.; Journal of Medicinal Chemistry, (1984), vol. 27, pp. 1127–1131.
Ashwood, et al.; Journal of Medicinal Chemistry, (1986), vol. 29, pp. 2194–2201.

Primary Examiner—Joseph Paul Brust
Attorney, Agent, or Firm—Jacobs & Jacobs

[57] ABSTRACT

Compounds of formula (I) and pharmaceutically acceptable salts thereof:

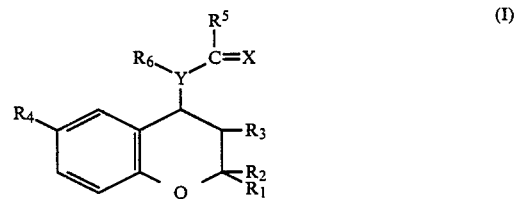

wherein: X, Y and $R_1$–$R_6$ are as defined have blood pressure lowering activity and K+ channel activator activity and are useful in the treatment of hypertension.

9 Claims, No Drawings

ACTIVE COMPOUNDS

The present invention relates to novel benzopyrans having pharmacological activity, to a process and intermediates for preparing them, to pharmaceutical compositions containing them, and to their use in the treatment of mammals.

European Patent Publications 76075, 93535, 95316, 107423, 120427, 126311, 126350, 126367 and 138134 disclose classes of compounds that are described as having blood pressure lowering activity or anti-hypertensive activity.

A class of compounds has now been discovered which are 4-substituted benzopyrans substituted in the 6-position by an alkyl group. In addition, such benzopyrans have been found to have blood pressure lowering activity, useful in the treatment of hypertension. In addition, these compounds are believed to be $K^+$ channel activators which indicates that they are of potential use in the treatment of disorders associated with smooth muscle contraction of the gastro-intestinal tract, respiratory system, uterus or urinary tract. Such disorders include irritable bowel syndrome and diverticular disease, reversible airways obstruction and asthma; premature labour; and incontinence. They are also indicated as of potential use in the treatment of cardiovascular disorders other than hypertension, such as congestive heart failure, angina, peripheral vascular disease and cerebral vascular disease. Accordingly, the present invention provides a compound of formula (I) or, when the compound of formula (I) contains a salifiable group, a pharmaceutically acceptable salt thereof:

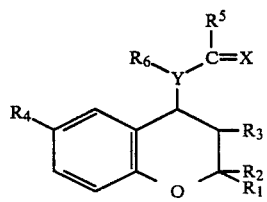

(I)

wherein:

$Y$ is N or (when $R_3$ is hydroxy, $C_{1-6}$ alkoxy or $C_{1-7}$ acyloxy) CH;

one of $R_1$ and $R_2$ is hydrogen or $C_{1-4}$ alkyl and the other is $C_{1-4}$ alkyl or $R_1$ and $R_2$ together are $C_{2-5}$-polymethylene;

$R_3$ is hydrogen, hydroxy, $C_{1-6}$ alkoxy or $C_{1-7}$ acyloxy;

$R_4$ is a $C_{3-8}$ cycloalkyl group or a $C_{1-6}$ alkyl group optionally substituted by a group $R_7$ which is hydroxy, $C_{1-6}$ alkoxy, amino optionally substituted by one or two $C_{1-6}$ alkyl groups; $C_{1-7}$ alkanoylamino, $C_{3-8}$-cycloalkyloxy, $C_{3-8}$ cycloalkylamino, or 1,3-dioxo-2-isoindoline;

When $Y$ is N, $R_5$ is hydrogen, $C_{1-6}$ alkyl optionally substituted by halogen, hydroxy, $C_{1-6}$ alkoxy, $C_{1-6}$ alkoxycarbonyl, carboxy or amino optionally substituted by one or two independent $C_{1-6}$ alkyl groups, or $C_{2-6}$ alkenyl, amino optionally substituted by a $C_{1-6}$ alkyl, $C_{3-8}$ cycloalkyl or $C_{1-6}$ alkenyl group or by a $C_{1-6}$ alkanoyl group optionally substituted by up to three halo atoms, by a phenyl group optionally substituted by $C_{1-6}$ alkyl, $C_{1-6}$ alkoxy or halogen, or aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups and $R_6$ is hydrogen or $C_{1-6}$ alkyl, or $R_5$ and $R_6$ together are $-CH_2-(CH_2)_n-Z-(CH_2)_m-$ wherein m and n are 0 to 2 such that m+n is 1 or 2 and Z is $CH_2$, O, S or NR wherein R is hydrogen, $C_{1-9}$ alkyl, $C_{2-7}$ alkanoyl, phenyl $C_{1-4}$-alkyl, naphthylcarbonyl, phenylcarbonyl or benzylcarbonyl optionally substituted in the phenyl or naphthyl ring by one or two of $C_{1-6}$ alkyl, $C_{1-6}$ alkoxy or halogen; mono- or bi-cyclic-heteroarylcarbonyl;

When $Y$ is CH, $R_5$ is $NR_8R_9$ wherein $R_8$ and $R_9$ are independently $C_{1-6}$ alkyl, $R_8$ is hydrogen and $R_9$ is $C_{1-6}$ alkyl or $R_8$ and $R_9$ together are $C_{4-5}$ polymethylene; or $R_6$ and $R_8$ together are $-(CH_2)_p-$ wherein p is 2 or 3, and $R_9$ is hydrogen or $C_{1-6}$ alkyl; or $R_5$ is $CH_2R_{10}$ wherein $R_{10}$ is hydrogen or $C_{1-5}$ alkyl; or $R_6$ and $R_{10}$ are $-(CH_2)_q-$ wherein q is 2 or 3;

$X$ is oxygen or sulphur; or $R_5$, $R_6$, $X$ and $Y$ (when N) together are tetrahydroisoquinolinone or tetrahydroisoquinolinthione, optionally substituted in the phenyl ring as defined for R above; the nitrogen-containing group in the 4-position being trans to the $R_3$ group when $R_3$ is hydroxy, $C_{1-6}$ alkoxy or $C_{1-7}$ acyloxy.

Y is preferably N.

Preferably, $R_1$ and $R_2$ are both $C_{1-4}$ alkyl, in particular both methyl.

When $R_3$ is $C_{1-6}$ alkoxy, preferred examples of $R_3$ include methoxy and ethoxy, of which methoxy is more preferred. When $R_3$ is $C_{1-7}$ acyloxy a preferred class of $R_3$ is unsubstituted carboxylic acyloxy, such as unsubstituted aliphatic acyloxy. However, it is more preferred that $R_3$ is hydroxy.

Examples of $R_4$ include cyclopropyl, cyclobutyl, cyclopentyl, cyclohexyl, cycloheptyl, methyl, ethyl, n- and iso-propyl, n-, iso-, sec- and tert-butyl, optionally substituted by a group $R_7^1$ which is hydroxy, $C_{1-4}$ alkoxy, amino optionally substituted by one or two $C_{1-4}$ alkyl groups, $C_{1-5}$ alkanoylamino, $C_{5-7}$ cycloalkyloxy or $C_{5-7}$ cycloalkyl. $C_{1-4}$ alkyl groups in $R_7^1$ may be methyl, ethyl, n- or iso-propyl, n-, iso-, sec-, or tert-butyl. $C_{5-7}$ cycloalkyl groups in $R_7^1$ may be cyclopentyl, cyclohexyl or cycloheptyl. $R_4$ is preferably $C_{5-7}$ cycloalkyl or $C_{1-4}$ alkyl.

When Y is N:

Examples of $R_5$, when $C_{1-6}$ alkyl, include methyl, ethyl, and n- and iso-propyl. Preferably such $R_5$ is methyl.

A sub-group of $R_5$, when $C_{1-6}$ alkyl substituted by halogen is $C_{1-6}$ alkyl substituted by chloro or bromo. Examples thereof include methyl or ethyl terminally substituted by chloro or bromo.

Examples of $R_5$, when $C_{1-6}$ alkyl substituted by hydroxy, include methyl or ethyl terminally substituted by hydroxy.

A sub-group of $R_5$, when $C_{1-6}$ alkyl substituted by alkoxy is $C_{1-6}$ alkyl substituted by methoxy or ethoxy. Examples thereof include methyl or ethyl terminally substituted by methoxy or ethoxy.

A sub-group of $R_5$, when $C_{1-6}$ alkyl substituted by $C_{1-6}$ alkoxycarbonyl is $C_{1-6}$ alkyl substituted by methoxycarbonyl or ethoxycarbonyl. Examples thereof include methyl or ethyl terminally substituted by methoxycarbonyl or ethoxycarbonyl.

Examples of $R_5$, when $C_{1-6}$ alkyl substituted by carboxy include methyl or ethyl terminally substituted by carboxy.

Examples of $R_5$ when alkyl substituted by amino optionally substituted by one or two independent $C_{1-6}$ alkyl groups include a group $(CH_2)_rNR_aR_b$ where r is 1 to 6, and $R_a$ and $R_b$ are each independently hydrogen or $C_{1-6}$ alkyl. Examples of r include 1 and 2, in particular 1. Preferably $R_a$ and $R_b$ are each independently selected from hydrogen and methyl. Examples of $R_5$, when $C_{2-6}$ alkenyl include vinyl, prop-1-enyl, prop-2-enyl, 1-methylvinyl, but-1-enyl, but-2-enyl, but-3-enyl, 1-methylenepropyl, or 1-methylprop-2-enyl, in both their E and Z forms where stereoisomerism exists.

Examples of $R_5$ when amino optionally substituted as hereinbefore defined include amino optionally substituted by a $C_{1-4}$ alkyl group as described for $R_7^1$, an allyl or trichloroacetyl group or by a phenyl group optionally substituted by one methyl, methoxy or chloro group or atom, in particular amino, methylamino, and phenylamino optionally substituted in the phenyl ring by one methyl, methoxy or chloro group or atom.

Examples of $R_5$ when aryl include phenyl and naphthyl, of which phenyl is preferred.

A sub-group of $R_5$ heteroaryl or heteroaryl in a Z moiety when NR is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl.

Examples of 9- or 10-membered bicyclic heteroaryl containing one, two or three heteroatoms which are selected from the class of oxygen, nitrogen and sulfur include benzofuranyl, benzothienyl, indolyl and indazolyl, quinolyl and isoquinolyl, and quinazonyl. Preferred examples of such groups include 2- and 3-benzofuryl, 2- and 3-benzothienyl, and 2- and 3-indolyl, and 2- and 3-quinolyl.

Preferably, the number of groups or atoms for optional substitution of aryl or heteroaryl is one, two, three or four.

Preferred examples of the groups or atoms for optional substitution of aryl or heteroaryl include methyl, methoxy, hydroxy, bromo, chloro, fluoro, nitro or cyano.

A sub-group of $R_5$ is phenyl or naphthyl or a 5- or 6-membered monocyclic or a 9- or 10-membered bicyclic heteroaryl, the phenyl, naphthyl or heteroaryl group being optionally substituted by one, two, three or four groups or atoms selected from the class of $C_{1-6}$ alkyl, $C_{1-6}$ alkoxy, halogen, (such as chloro, bromo or, in particular, fluoro), trifluoromethyl, nitro or cyano.

A preferred subgroup of phenyl optionally substituted as hereinbefore defined is phenyl, 4-substituted phenyl, 3-substituted phenyl, 3,4-disubstituted phenyl and 3,4,5-trisubstituted phenyl.

A preferred sub-group of 5- or 6-membered monocyclic or 9- or 10-membered bicyclic heteroaryl optionally substituted as hereinbefore defined is unsubstituted or mono-substituted 5- or 6-membered monocyclic or 9- or unsubstituted 5- or 6-membered monocyclic or 9- or 10-membered bicyclic heteroaryl.

$R_5$ and $R_6$, when together are $-CH_2-(CH_2)_n-Z-(CH_2)_m-$ as defined the resulting radical substituting the benzopyran in the 4-position is preferably either pyrrolidonyl or piperidonyl.

When Z is other than $CH_2$, m is often 0 or 1 and n is often 0 or 1. Suitable examples of R when Z is NR include hydrogen, methyl, ethyl, n- and iso-propyl, n-, iso-, sec- and tert-butyl, benzyl, phenylcarbonyl or benzylcarbonyl optionally substituted in the phenyl ring by methyl, methoxy, chloro or bromo; furylcarbonyl, thienylcarbonyl, pyrrolylcarbonyl or indolylcarbonyl. Preferably R is hydrogen, methyl, n-butyl, acetyl, benzyl, benzylcarbonyl, phenylcarbonyl or furylcarbonyl. Most preferably R is methyl.

Preferred examples of $R_5$ and $R_6$ are $R_5$ methyl and $R_6$ hydrogen and $R_5$ and $R_6$ together are $C_3$ or $C_4$ polymethylene.

When Y is CH, $R_6$ is preferably hydrogen and $R_5$ is $NR_8R_9$. Examples of $R_8$ and $R_9$, include hydrogen (for $R_8$), methyl, ethyl, n- and iso-propyl, and n-, iso-, sec- and t-butyl, $C_4$ or $C_5$ polymethylene or $R_8$ together with $R_6$ is $-(CH_2)_2-$ or $-(CH_2)_3-$, and $R_9$ is hydrogen or an alkyl group as described above. Preferably $R_8$ and $R_9$ are each methyl or $R_6CHCXNR_8R_9$ forms a pyrrolidone or piperidone ring and $R_9$ is methyl.

Preferably, X is oxygen.

Examples of a pharmaceutically acceptable salt of a compound of formula (I), when the compound contains a salifiable group which is an optionally substituted amino group, include acid addition salts such as the hydrochloride and hydrobromide salts. Such a salifiable group may be within an $R_4$ or $R_5$ group. A carboxy group within $R_5$ may also be salifiable to form metal salts, such as alkali metal salts, or optionally substituted ammonium salts.

The compounds of formula (I) may also exist as hydrates and these are included wherever a compound of formula (I) or a salt thereof is herein referred to.

The compounds of formula (I), as asymmetric, and, therefore, can exist in the form of optical isomers. The present invention extends to all such isomers individually and as mixtures, such as racemates.

Examples of compounds of formula (I) include the compounds prepared in the Examples hereinafter.

The present invention also provides a process for the preparation of a compound of formula (I) or, when the compound of formula (I) contains a salifiable group, a pharmaceutically acceptable salt thereof, which comprises;

(i) (When Y is N) acylating a compound of formula (II):

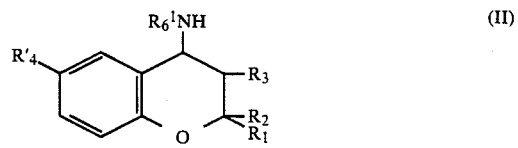

wherein $R_4'$ is $R_4$ or a group convertible thereto; $R_1$ $R_2$ and $R_3$ are as hereinbefore defined, and $R_6^1$ is hydrogen or $C_{1-6}$ alkyl, the $R_6^1$NH group being trans to the $R_3$ group, (a) with an acylating agent of formula (III):

$$R_{11}-CO-L_1 \qquad (III)$$

wherein $L_1$ is a leaving group, and $R_{11}$ is hydrogen, $C_{1-6}$ alkyl optionally substituted by halogen, hydroxy, $C_{1-6}$ alkoxy, $C_{1-6}$ alkoxycarbonyl, carboxy or amino optionally substituted as hereinbefore defined for $R_5$, $C_{2-6}$ alkenyl or optionally substituted aryl or heteroaryl as hereinbefore defined for $R_5$, or a group convertible to $R_5$ as hereinbefore defined, and thereafter, when $R_6$ is hydrogen and $R_{11}$ is $Q(CH_2)_z$—, where z is 3 or 4; and Q is a leaving group, cyclising the resultant compound;

(b) with a compound of formula (IV)

$$X=C=N.R_{12} \qquad (IV)$$

wherein $R_{12}$ is hydrogen, $C_{1-6}$ alkyl, $C_{1-6}$ alkenyl, $C_{1-6}$ alkanoyl optionally substituted by up to three halo atoms, or phenyl optionally substituted by $C_{1-6}$ alkyl, $C_{1-6}$ alkoxy or halogen; and X is oxygen or sulphur, and thereafter when $R_{12}$ is hydrogen, optionally converting $R_{12}$; or (ii) where, in the resultant compound of formula (I), Y is N and $R_5$ and $R_6$ are joined together, or Y is CH, reacting a compound of formula (V):

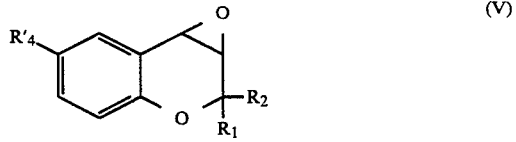

wherein $R_4'$, $R_1$ and $R_2$ are as hereinbefore defined, with a compound of formula (VI):

$$R_{14}YHCOR_{13} \qquad (VI)$$

or an anion thereof (when Y is CH); wherein (when Y is N), $R_{13}$ and $R_{14}$ together are —$CH_2$—($CH_2$)$_n$—Z—($CH_2$)$_m$— or $R_{14}$YHCOR$_{13}$ is tetrahydroisoquinolinone; or (when Y is CH) $R_{13}$ is $NR_8'R_9$ or $CHR_{10}CO_2R_{15}$ wherein $R_{15}$ is $C_{1-6}$ alkyl or benzyl, $R_8'$ is $R_8$ or an amino protecting group and the remaining variables are as hereinbefore defined; and thereafter, if necessary, converting $R_{13}$ to $R_7$, converting $R_8'$ to $R_8$; optionally converting $R_3$ in the resulting compound into another $R_3$; converting $R_4'$ to $R_4$ and optionally thiating the $R_6$—Y—CO—$R_5$ group in the resulting compound to give a compound wherein X is sulphur; and when the resulting compound of formula (I) contains a salifiable group, optionally forming a pharmaceutically acceptable salt thereof.

In the process variant (i) (a) acylation of a compound of formula (II) with an acylating agent of formula (III), the leaving group $L_1$ is a group that is displaceable by a primary or secondary amino nucleophile. Examples of such a group include $C_{1-4}$ alkanoyloxy, and halogen, such as chloro and bromo. When the leaving group $L_1$ is either of these examples, the acylating agent of formula (III) is either an acid anhydride or an acid halide. When it is an acid anhydride, it may be a mixed or simple anhydride. If it is a mixed anhydride, it may be prepared in situ from a carboxylic acid and an acid halide, although this is less preferred than using the halide itself.

In process variant (i) (a), when $R_5$ in the desired compound of formula (I) is an $R_5$ optionally substituted amino-substituted alkyl group as hereinbefore defined, it is preferred that $R_{11}$ is a group convertible to the $R_5$ substituted alkyl group as hereinbefore defined, in particular that it is $C_{1-6}$ alkyl substituted by halo, especially bromo. The $R_{11}$ halo substituent in the resultant compound of process variant (i) (a) may be converted to an $R_5$ substituent which is amino optionally substituted as hereinbefore defined by a conventional amination reaction with ammonia or a corresponding alkyl- or dialkylamine.

Less favourably $R_{11}$ may be $C_{1-6}$ alkyl substituted by protected amino, protected $C_{1-6}$ alkylamino or amino substituted by two independent $C_{1-6}$ alkyl groups, it being necessary to protect the $R_{11}$ amino function in process variant (i) (a).

When the acylating agent of formula (III) is an acid anhydride, the acylation of the compound of formula (II) may be carried out in the presence of an acid acceptor, such as sodium acetate, optionally using the anhydride as the solvent.

When the acylating agent of formula (III) is an acid halide, the acylation of the compound of formula (II) is, preferably, carried out in a non-aqueous medium, such as dichloromethane, in the presence of an acid acceptor, such as triethylamine, trimethylamine, pyridine, picoline or calcium, potassium or sodium carbonate.

When $R_3$ in a compound of formula (II) is hydroxy, there is a risk of a side-reaction between the hydroxy group and the acylating agent of formula (III). However, the reaction may be carried out under controlled conditions such that only the $R_6^1$YH— is acylated, for example, by using a $C_{2-9}$ acyloxy group as the leaving group $L_1$, in the acylating agent of formula (III) in the manner as previously described for an acid anhydride, and/or effecting the reaction at relatively low temperature, e.g. at below 10° C. Alternatively $R_3$ may be $C_{1-7}$ acyloxy in a compound of formula (II), although less preferably if $R_3$ in the resultant compound of formula (I) is to be hydroxy, and, after reaction with the acylating agent of formula (III), be converted into hydroxy, as described hereinafter.

When $R_9$ is $Q(CH_2)_z$ where the variables are as hereinbefore defined, the leaving group Q is a group that is displaceable by a secondary amino nucleophile adjacent to a carbonyl function. A preferred example is chloro.

The cyclisation reaction when $R_{11}$ is $Q(CH_2)_z$ where the variables are as hereinbefore defined is preferably carried out in an inert solvent such as dimethylformamide.

In process variant (i) (b), when $R_{12}$ in a compound of formula (IV) is $C_{1-6}$ alkyl, $C_{1-6}$ alkanoyl optionally substituted as hereinbefore defined, or phenyl optionally substituted as hereinbefore defined, the reaction between the compounds of formulae (II) and (IV) is, preferably, carried out in a solvent, such as methylene chloride, at below room temperature, in particular below 10° C.

When $R_{12}$ is hydrogen, the reaction between the compounds of formulae (II) and (IV) is, preferably, carried out using a corresponding alkali metal cyanate or thiocyanate, for example that of sodium or potassium, in an optionally methanolic aqueous medium acidified with a mineral acid, such as dilute hydrochloric acid. A slightly elevated temperature such as 50° to 90° C. is apt.

In the process variant (ii) when Y is N, reaction of a compound of formula (V) with a compound of formula (VI), it is particularly preferred that the reaction is carried out under basic conditions so as to facilitate the formation of the anion of the compound of formula (VI), for example, in the presence of sodium hydride.

In the process variant (ii) when Y is CH, the reaction is preferably carried out in a solvent such as tetrahydrofuran at a temperature of −70° C. to reflux, depending on the anion of the compound of formula (VI). The anion is generated by use of a base, such as lithium diisopropylamide.

An intermediate compound wherein $R_{13}$ is $CHR_{10}CO_2R_{15}$ may be converted to a compound of formula (I) wherein $R_7$ is $CH_2R_{10}$, by deesterification followed by decarboxylation.

Deesterification may be effected conventionally, the most appropriate method depending to some extent on the nature of the group $R_{14}$. However, basic reaction conditions will generally be applicable. The process conditions described hereinafter for the decarboxylation in the presence of base are in general suitable for this deesterification.

When $R_{14}$ is, for example, a tert-butyl group, deesterification may also be effected conventionally in the presence of acid such as trifluoroacetic acid or aqueous hydrochloric acid. Reaction may be effected at ambient temperature or a slightly higher temperature.

When $R_{14}$ is for example a benzyl group, deesterification may also be effected conventionally by hydrogenolysis, for example by transition-metal catalysed hydrogenation, such as that using palladium/charcoal.

The decarboxylation is conveniently effected by treatment with a moderately strong base optionally in an aqueous reaction medium. Examples of bases for the reaction include inorganic bases such as sodium hydroxide. Examples of reaction media include water, usually in admixture with a water-miscible solvent such that the compound is soluble therein. Examples include aqueous alcohols such as aqueous ethanol and aqueous polyethers such as aqueous dioxan. Reaction is conveniently effected at a moderately elevated temperature, such as 50° to 150° C., conveniently at the boiling point of the reaction medium.

Alternatively the decarboxylation may be effected by heating to a non-extreme temperature, for example 60° to 150° C. in an inert solvent, such as benzene, toluene or xylene, for example at solvent boiling point.

Spontaneous decarboxylation may occur under the reaction conditions for the deesterification. Even where this is not the case, it is convenient to decarboxylate the $CHR_{10}CO_2H$ compound in situ without isolation. It is especially convenient to carry out the conversion $CHR_{10}CO_2R_{12}$ to $CH_2R_{10}$ as a single-step one-pot process, by treatment with a moderately strong base optionally in an aqueous reaction medium. Suitable conditions are as hereinbefore described for decarboxylation.

The reaction of the compounds of formulae (II) with (III) or (IV) results in a compound of formula (I) wherein $R_3$ is hydroxy, $C_{1-6}$ alkoxy or $C_{1-7}$ acyloxy, whereas the reaction of the compounds of formulae (V) and (VI) results in a compound of formula (I) wherein $R_3$ is hydroxy. Examples of an optional conversion of $R_3$ in a compound of formula (I) into another $R_3$ are generally known in the art. For example, when $R_3$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent in the presence of antacid acceptor. Alternatively, when $R_3$ is $C_{1-7}$ acyloxy or $C_{1-6}$ alkoxy, it may be converted into hydroxy by conventional hydrolysis with, for example, dilute mineral acid.

Suitable conversions of $R_4'/R_4$ include conventional alkylation or acylation of $R_7$ when hydroxy or optionally monosubstituted amino. It is usually preferred, however, that such conversions are carried out at an earlier stage.

$R_4'$ may be cyano which may be converted to $R_4$ when a substituted methyl group, by conventional methods as described in the Examples hereinafter, for example, reduction to give an aminomethyl group.

The optional thiation of the $R_6$—Y—CO—$R_5$ group in a compound of formula (I) to give another compound of formula I, wherein X is sulphur, is, preferably, carried out with conventional thiation agents, such as hydrogen sulphide, phosporous pentasulphide and Lawesson's reagent (p-methoxyphenylthiophosphine sulphide dimer). The use of hydrogen sulphide and phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is, preferably, carried out under reflux in a dry solvent, such as toluene or methylene chloride.

The optional formation of a pharmaceutically acceptable salt, when the resulting compound of formula (I) contains a salifiable group, may be carried out conventionally.

A compound of formula (II) wherein $R_3$ is hydroxy, $C_{1-6}$ alkoxy or $C_{1-7}$ acyloxy may be prepared by reacting a compound of formula (V), as hereinbefore defined, with a compound of formula (VII):

$$R_6^1NH_2 \qquad\qquad\qquad\qquad (VII)$$

wherein $R_6^1$ is as defined hereinbefore; and optionally converting $R_3$ hydroxyl in the resulting compound of formula (II) into $R_3$ when $C_{1-6}$ alkoxy or $C_{1-7}$ acyloxy.

The reaction is normally carried out in a solvent, such as a $C_{1-4}$ alcohol, in particular methanol, ethanol or propanol at an ambient or an elevated temperature, for example 12° to 100° C. The reaction proceeds particularly smoothly if carried out in ethanol under reflux.

The resulting compound of formula (II) may be removed from the reaction mixture by removal of the solvent, for example, by evaporation under reduced pressure. Any epoxide impurity may be removed conventionally, for example by chromatography.

The optional conversion of the hydroxy group for $R_3$ in the resulting compound of formula (II) into a $C_{1-6}$ alkoxy or $C_{1-7}$ acyloxy group may be carried out as described hereinbefore in relation to the corresponding conversion of $R_3$ in a compound of formula (I).

A compound of formula (II) wherein $R_3$ is hydrogen may be prepared by known methods, for example as described in *Khim. Geterot. Soed* 5 (3), 434, 1969.

A compound of formula (V) may be prepared by reacting a compound of formula (VIII):

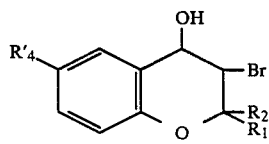

wherein $R_1$ and $R_2$ are as hereinbefore defined, the bromine atom being trans to the hydroxy group, with a base, such as potassium hydroxide, in a solvent, such as ether or aqueous dioxan.

A compound of formula (VIII) may be prepared by reacting a compound of formula (IX):

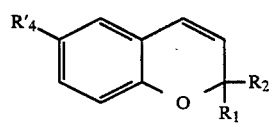

wherein $R_1$ and $R_2$ are as hereinbefore defined, with N-bromosuccinimide in a solvent, such as aqueous dimethyl sulphoxide.

A compound of formula (IX) may be prepared in accordance with analogous processes to those described in the aforementioned European Patent publications, i.e. by the process depicted below:

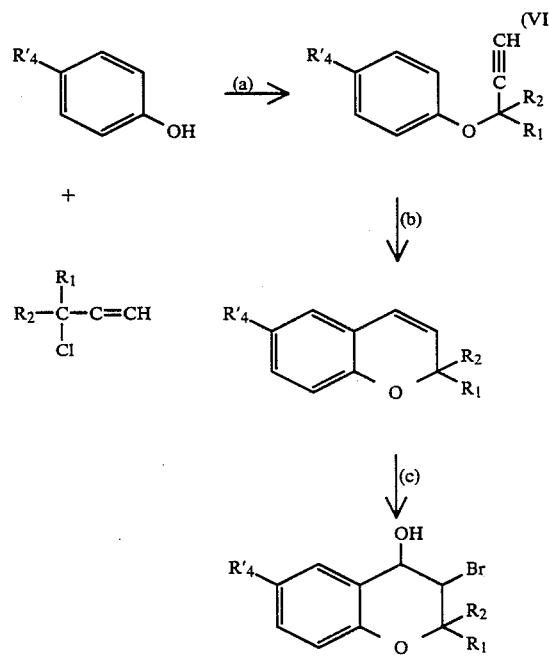

(a) Reflux; acetone; $K_2CO_3$/KI; or a phase transfer catalytic method with optional sonification;
(b) Heat in o-dichlorobenzene or N,N-diethylaniline;
(c) N-bromosuccinimide/dimethylsulphoxide/water;

As mentioned previously, some of the compounds of formula (I) may exist in optically active forms, and the processes of the present invention produce mixtures of such forms. The individual enantiomers may be resolved by conventional methods.

It is preferred that the compounds of formula (I) are isolated in pharmaceutically acceptable form.

The intermediates of formulae (II) represent part of the present invention. The intermediates of formulae (III), (IV), (V), (VI), (VII), (VIII) and (IX) are known or may be prepared in accordance with an appropriate known process.

As mentioned previously, the compounds of formula (I) have been found to have blood-pressure lowering activity. They are therefore useful in the treatment of hypertension. They are also believed to be of potential use in the treatment of other disorders hereinbefore referred to.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive pharmaceutical composition which comprises an anti-hypertensive effective amount of a compound of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration. A composition may be in the form of spray, aerosol or other conventional method of inhalation, for treating respiratory tract disorders.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compounds of the present invention, the severity of the hypertension being treated and the weight of the sufferer. However, a unit dose form of a composition of the invention may contain from 1 to 100 mg of a compound of the invention and more usually from 1 to 50 mg, for example 1 to 25 mg such as 1, 2, 5, 10, 15 or 20 mg. Such compositions may be administered from 1 to 6 times a day, more usually from 1 to 4 times a day, in a manner such that the daily dose is from 1 to 200 mg for a 70 kg human adult and more particularly from 1 to 100 mg.

No toxicological effects are indicated at the aforementioned dosage ranges.

The present invention further provides a compound of formula (I) or a pharmaceutically acceptable salt thereof for use in the treatment or prophylaxis of hypertension.

The following descriptions relate to the preparation of intermediates and the following example relates to the preparation of a compound of formula (I).

All temperatures therein are in °C.

DESCRIPTION 1

2,2-Dimethyl-6-t-butyl-2H-1-benzopyran (D1)

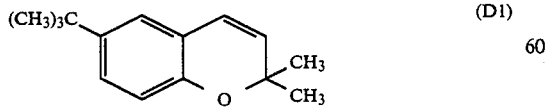

(D1)

4-t-Butylphenol (10 g) and sodium hydroxide (3.99 g) were added to a stirred mixture of water (60 ml) and dichloromethane (60 ml) followed by benzyltrimethylammonium hydroxide (40% solution in methanol, 150 ml) and 3-chloro-3-methyl-butyne (13.65 g). After stirring at ambient temperature for 11 days, the layers were separated and the aqueous layer extracted with chloroform. The combined organic extracts were concentrated in vacuo and the residue dissolved in diethyl ether. The solution was washed with water, 10% sodium hydroxide solution, then brine, and dried over magnesium sulphate. Removal of drying agent and solvent gave 3-methyl-3-(4-t-butylphenoxy)-but-1-yne as a yellow oil (13.35 g).

A solution of this product in ortho-dichlorobenzene (27 ml) was heated under reflux, under nitrogen, for 12 hours. Solvent was removed in vacuo, and the residue chromatographed on silica gel eluted with ethyl acetate:60–80 petroleum ether (1:19) to give the desired chromene as a brown oil (3.4 g) having:

$^1$H nmr (CDCl$_3$)
1.27 (s, 9H)
1.40 (s, 6H)
5.50 (d, J=9 Hz, 1H)
6.25 (d, J=9 Hz, 1H)
6.60 (d, J=8 Hz, 1H)
7.10 (m, 2H)

DESCRIPTION 2

Trans-6-(t-butyl)-3,4-dihydro-2,2-dimethyl-3-bromo-4-hydroxy-2H-1-benzopyran (D2)

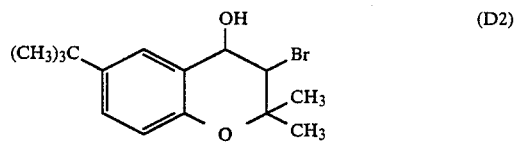

(D2)

A solution of 2,2-dimethyl-6-t-butyl-2H-1-benzopyran (3.4 g) in dimethyl sulphoxide (35 ml) and water (3 ml) was treated with N-bromosuccinimide (3.1 g) and the mixture stirred vigorously for 1 hour. Water was added, and the mixture extracted into ethyl acetate. The combined organic extracts were washed with water, then brine, and dried over magnesium sulphate. Removal of drying agent and solvent gave the required bromohydrin (0.88 g) having M.pt. 122°–3° C.
$^1$H nmr (CDCl$_3$)
1.30 (s, 9H)
1.40 (s, 3H)
1.58 (s, 3H)
2.44 (d, J=6 Hz, 1H)
4.14 (d, J=10 Hz, 1H)
4.90 (dd, J=10, 6 Hz, 1H)
6.73 (d, J=9 Hz, 1H)
7.25 (dd, J=9, 3 Hz, 1H)
7.48 (d, J=3 Hz, 1H).
Mass spectrum: Found M+ 312.0723; C$_{15}$H$_{21}$O$_2$Br requires M+ 312.0725.

DESCRIPTION 3

6-t-Butyl-3,4-epoxy-3,4-dihydro-2,2-dimethyl-2H-1-benzopyran (D3)

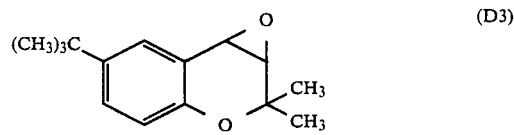

(D3)

A mixture of trans-6-t-butyl-3,4-dihydro-2,2-dimethyl-3-bromo-4-hydroxy-2H-1-benzopyran (0.88 g) and potassium hydroxide pellets (0.88 g) in dry diethyl ether (88 ml) was stirred vigorously for 4 days. Filtration and removal of solvent in vacuo gave the desired epoxide as a brown oil (0.52 g) having $^1$H nmr (CDCl$_3$)
1.20 (s, 3H)
1.30 (s, 9H)
1.55 (s, 3H)
3.40 (d, J=4 Hz, 1H)
3.80 (d, J=4 Hz, 1H)
6.60 (d, J=9 Hz, 1H)
7.13 (dd, J=9, 3 Hz, 1H)
7.20 (d, J=3 Hz, 1H).

Mass spectrum: Found M+ 232.1463; C$_{15}$H$_{20}$O$_2$ requires M+ 232.1465.

DESCRIPTION 4

2,2-Dimethyl-6-i-propyl-2H-1-benzopyran (D4)

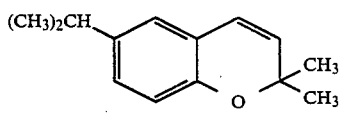
(D4)

The title compound (2.2 g) was prepared from 4-i-propyl phenol (9.07 g) as in Description 1.

$^1$H nmr (CDCl$_3$)
1.20 (d, J=7 Hz, 6H)
1.40 (s, 6H)
2.80 (septet, 1H)
5.45 (d, J=10 Hz, 1H)
6.20 (d, J=10 Hz, 1H)
6.70–7.30 (m, 3H)

DESCRIPTION 5

Trans-6-(i-propyl)-3,4-dihydro-2,2-dimethyl-3-bromo-4-hydroxy-2H-1-benzopyran (D5)

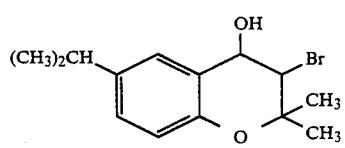
(D5)

2,2-Dimethyl-6-i-propyl-2H-1-benzopyran (2.2 g) was reacted as in Description 2 to give the title compound (2.7 g) as an oil having $^1$H nmr (CDCl$_3$)
1.20 (d, J=7 Hz, 6H)
1.37 (s, 3H)
1.55 (s, 3H)
2.80 (septet, J=7 Hz, 1H)
4.03 (d, J=9 Hz, 1H)
4.80 (m, 1H)
6.55 (d, J=8 Hz, 1H)
6.80–7.20 (m, 2H).

Mass spectrum: Found M+ 298.0563, 300.0553; C$_{14}$H$_{19}$O$_2$Br requires 298.0568, 300.0548.

DESCRIPTION 6

Trans-6-(i-propyl)-3,4-epoxy-3,4-dihydro-2,2-dimethyl-2H-1-benzopyran (D6)

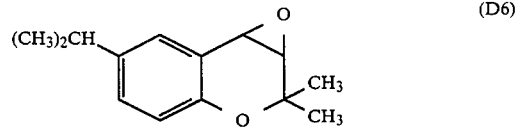
(D6)

Trans-6-(i-propyl)-3,4-dihydro-2,2-dimethyl-3-bromo-4-hydroxy-2H-1-benzopyran (2.7 g) was reacted as in Description 3 to give the title compound (1.89 g) as a pale brown oil having $^1$H nmr (CDCl$_3$)
1.20 (d, J=7 Hz, 6H)
1.20 (s, 3H)
1.50 (s, 3H)
2.80 (septet, J=7 Hz, 1H)
3.40 (d, J=4 Hz, 1H)
3.80 (d, J=4 Hz, 1H)
6.60 (d, J=8 Hz, 1H)
6.80–7.30 (m, 2H).

Mass spectrum: Found M+ 218.1325; C$_{14}$H$_{18}$O$_2$ requires 218.1307.

DESCRIPTION 7 trans-4-Amino-3,4-dihydro-2,2,6-trimethyl-2H-1-benzopyran-3-ol (D7)

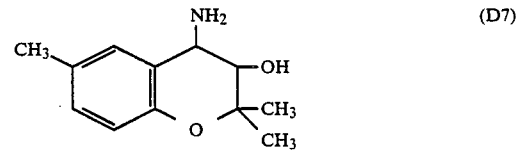
(D7)

A solution of 3,4-epoxy-3,4-dihydro-2,2,6-trimethyl-2H-1-benzopyran (7 g, see J. Med. Chem. 26, 1582, 1983) in concentrated ammonia solution (90 ml) and ethanol (160 ml) was stirred at room temperature for 5 days. Evaporation of solvent gave the title compound (7 g) as a crude solid which was used directly, without purification.

NMR (CDCl$_3$) δ
1.15 (s, 3H)
1.38 (s, 3H)
2.25 (s, 3H)
3.23 (d, J=9 Hz, 1H)
3.57 (d, J=9 Hz, 1H)
6.68 (d, J=8 Hz, 1H)
6.87 (q, J=8, 2 Hz, 1H)
7.02 (narrow m, 1H).

DESCRIPTION 8 trans-4-Amino-3,4-dihydro-2,2-dimethyl-6-isopropyl-2H-1-benzopyran-3-ol (D8)

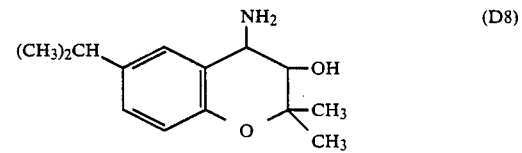
(D8)

The epoxide of description 6 (2.5 g) was stirred in ethanol (125 ml) and 0.88 ammonia solution (120 ml) at room temperature for 20 h. The solution was evaporated and partitioned between ethyl acetate and water. The organic layer was washed with brine and dried over anhydrous magnesium sulphate, filtered and evaporated to give the title compound (1.49 g) which was used directly.

NMR (CDCl$_3$) δ
1.17 (s, 3H)
1.20 (d, J=6 Hz, 6H)
2.43 (m, 3H, exchangeable with D$_2$O) overlapped with 2.80 (m, J=6 Hz, 5 lines visible, 1H)
3.28 (d, J=9 Hz, 1H)
3.61 (d, J=9 Hz, 1H)
6.59 (d, J=8 Hz, 1H)
6.92 (q, J=8, 2 Hz, 1H)
7.05 (narrow m, 1H).

DESCRIPTION 9

6-Ethyl-2,2-dimethyl-2H-1-benzopyran (D9)

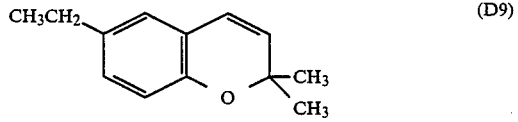

To 4-ethylphenol (8.15 g) and sodium hydroxide pellets (3.99 g) stirred in dichloromethane (60 ml) and water (60 ml) was added benzyltrimethylammonium hydroxide (40% solution in methanol, 150 ml) and 3-chloro-3-methyl-butyne (13.65 g). The reaction mixture was stirred at room temperature for 2 weeks. The layers were separated, and the aqueous layer extracted with chloroform. The combined organic extracts were evaporated, and the residue taken up in ether and washed with 5N hydrochloric acid, 10% aqueous sodium hydroxide, water, and brine and dried over anhydrous magnesium sulphate. Removal of drying agent and solvent gave an oil (9.9 g) which was refluxed in NN-diethylaniline (50 ml) under nitrogen for 2.75 h. The mixture was cooled, and poured into cooled 5N hydrochloric acid (100 ml) and the solution extracted with ether. The organic phase was washed with 5N hydrochloric acid and brine and dried over anhydrous magnesium sulphate. Removal of drying agent and solvent left a brown oil (9.0 g) which was chromatographed on silica gel and eluted with 5% ethyl acetate-pentane to give the title benzopyran (2.36 g) as an oil.

Mass spectrum (EI) M+ at m/z 188.1192.
C$_{13}$H$_{16}$O requires 188.1201.

DESCRIPTION 10 trans-3-Bromo-6-ethyl-3,4-dihydro-2,2-dimethyl-2H-1-benzopyran-4-ol (D10)

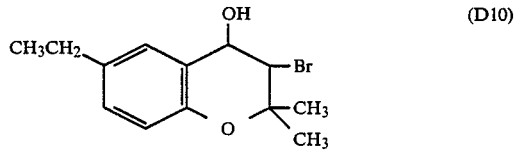

To a solution of 6-ethyl-2,2-dimethyl-2H-1-benzopyran (2.36 g) in dimethyl sulphoxide (20 ml) and water (2 ml) was added N-bromosuccimimide (2.46 g) and the mixture stirred for 1.5 h. Water was added and the mixture extracted with ethyl acetate. The organic extract was washed with water, brine and dried over anhydrous magnesium sulphate. Removal of drying agent and solvent left the title bromohydrin as a brown oil (3.0 g).

NMR (CDCl$_3$+D$_2$O)
1.22 (t, J=7 Hz, 3H)
1.40 (s, 3H)
1.60 (s, 3H)
2.58 (q, J=7 Hz, 2H)
4.14 (d, J=9 Hz, 1H)
4.91 (d, J=9 Hz, 1H)
6.72 (d, J=8 Hz, 1H)
6.95–7.40 (m, 2H).

DESCRIPTION 11

3,4-Epoxy-6-ethyl-3,4-dihydro-2H-1-benzopyran (D11)

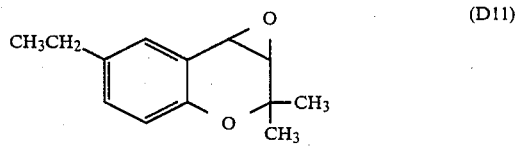

The bromohydrin of description 10 (3.0 g) and potassium hydroxide pellets (3.1 g) were stirred vigorously in diethyl ether (500 ml) for 6 days at room temperature. Filtration and evaporation gave the title epoxide (1.91 g) as a brown oil, which was used directly in example 13.

DESCRIPTION 12

2,2-Dimethyl-6-cyclopentyl-2H-1-benzopyran (D12)

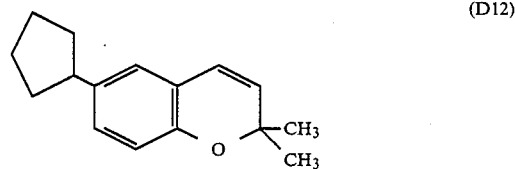

4-Cyclopentylphenol (10.0 g), and sodium hydroxide pellets (3.7 g) were stirred in water (60 ml) and dichloromethane (60 ml). Benzyltrimethylammonium hydroxide (75 ml, 40% solution in methanol) was added to the solution, followed by 3-chloro-3-methylbutyne (12.63 g) and the reaction mixture stirred under reflux condenser, with sonication. The layers were separated, and the aqueous phase extracted with chloroform. The combined organic layers were evaporated, and the residue taken up in ether. The ether solution was washed with 10% sodium hydroxide solution, and brine and dried over anhydrous magnesium sulphate. Filtration and evaporation gave a pale brown oil (10.89 g) which was refluxed in o-dichlorobenzene (22 ml) under nitrogen for 2 h. Evaporation and chromatography of the resulting brown oil (9.3 g) gave the title benzopyran (4.18 g).

NMR (CDCl$_3$) δ
1.42 (s, 6H)
1.47–1.86 (m, 6H)
2.03 (m, 2H)
2.90 (m, 1H)
5.57 (d, J=10 Hz, 1H)
6.28 (d, J=10 Hz, 1H)
6.68 (d, J=8 Hz, 1H)

6.83 (d, J=2 Hz, 1H)
6.97 (q, J=8, 2 Hz, 1H).

DESCRIPTION 13 trans-3-Bromo-3,4-dihydro-2,2-dimethyl-6-cyclopentyl-2H-1-benzopyran-4-ol (D13)

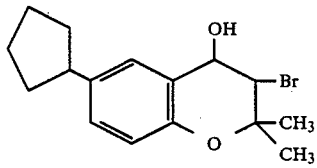

To the benzopyran of description 12 (4.08 g) in dimethyl sulphoxide (40 ml) and water (4 ml) was added N-bromosuccinimide (3.49 g) and the reaction mixture stirred at room temperature for 2 h. before the addition of further N-bromosuccinimide (0.35 g), and an additional 0.5 h of stirring. Extraction via ethyl acetate yielded a yellow solid (5.36 g) which was usd directly to form the epoxide of description 14.

Mass spectrum (EI) M+ at m/z 324.0727.
$C_{16}H_{21}O_2Br$ requires 324.0726.

DESCRIPTION 14

3,4-Epoxy-3,4-dihydro-2,2-dimethyl-6-cyclopentyl-2H-1-benzopyran (D14)

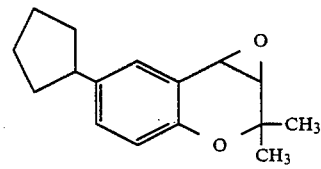

The bromohydrin of description 13 (5.0 g) and potassium hydroxide pellets (5.0 g) were vigorously stirred in ether (500 ml) at room temperature for 6 days. Filtration and evaporation gave the epoxide of this description as a pale brown oil (3.12 g).

NMR (CDCl₃) δ
1.24 (s, 3H)
1.56 (s, 3H)
1.52–1.86 (series of m, 6H)
2.04 (m, 2H)
2.93 (symmetrical m, 1H)
3.47 (d, J=4 Hz, 1H)
3.87 (d, J=4 Hz, 1H)
6.72 (d, J=8 Hz, 1H)
7.09 (q, J=8, 2 Hz, 1H)
7.18 (d, J=2 Hz, 1H).

EXAMPLE 1 trans-6-Methyl-2,2-dimethyl-4-(2-oxopiperidinyl)-2H-1-benzopyran-3-ol (E1)

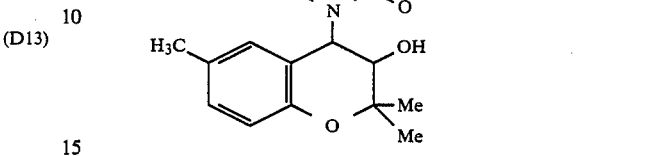

2-Piperidone (1.0 g) was added to a stirred suspension of sodium hydride (300 mg) in dry dimethylsulphoxide (20 ml) and the mixture stirred for 1 hour, under nitrogen. Then a solution of 6-methyl-3,4-epoxy-3,4-dihydro-2,2-dimethyl-2H-1-benzopyran (1.9 g) in dimethylsulphoxide (10 ml) was added and the mixture stirred for 16 hours, at room temperature. Water was added, and the mixture extracted into ethyl acetate. The combined organic extracts were washed with water, then brine, and dried over magnesium sulphate. Removal of solvent in vacuo, and recrystallisation of the residue from ethyl acetate: 60°–80° petroleum-ether (1:9) gave the title compound as colourless prisms (400 mg, 15%) having m.p. 162°–4° C.;

¹H n.m.r. (CDCl₃)
1.25 (s, 3H)
1.50 (s, 3H)
1.80 (m, 4H)
2.25 (s, 3H)
2.60 (t, J=8 Hz, 2H)
3.00 (m, 2H)
3.60 (br s, OH)
3.75 (d, J=10 Hz, 1H)
5.85 (d, J=10 Hz, 1H)
6.80 (m, 3H).

Anal. Found: C 70.53%, H 8.13%, N 4.88%; $C_{17}H_{23}NO_3$ requires: C 70.56%, H 8.01%, N 4.84%.

EXAMPLE 2 trans-6-t-Butyl-2,2-dimethyl-4-(2-oxo-pyrrolidinyl)-2H-1-benzopyran-3-ol (E2)

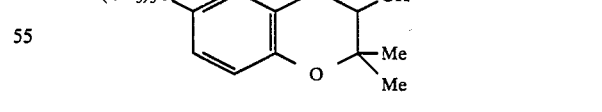

An 80% dispersion of sodium hydride in oil (0.067 g) was added to a stirred solution of trans-6-t-butyl-3,4-epoxy-3,4-dihydro-2,2-dimethyl-2H-1-benzopyran (0.52 g) and 2-pyrrolidinone (0.19 g) in dry dimethyl sulphoxide (25 ml), and the mixture stirred for 20 hours under nitrogen. Water was added, and the mixture extracted into ethyl acetate. The combined organic extracts were washed with water, then brine, and dried over magnesium sulphate. Removal of solvent in vacuo and recrystallisation of the residue from ethyl acetate/60–80 petroleum ether gave the title compound as fine white needles (0.11 g) having M.pt. 227°–8° C.

$^1$H nmr (CDCl$_3$)

1.25 (s, 9H)
1.27 (s, 3H)
1.49 (s, 3H)
1.95–2.20 (m, 2H)
2.57 (m, 2H)
3.00–3.15 (m, 2H)
3.20–3.30 (m, 1H)
3.73 (dd, J=11,6 Hz, 1H)
5.30 (d, J=11 Hz, 1H)
6.75 (d, J=9 Hz, 1H)
6.90 (d, J=3 Hz, 1H)
7.20 (dd, J=9,3 Hz, 1H).

Mass spectrum: Found M$^+$ 317.1992; C$_{19}$H$_{27}$NO$_3$ requires 317.1991.

Analysis: Found C, 71.46; H, 8.43; N, 4.17; C$_{19}$H$_{27}$NO$_3$ requires C, 71.89; H, 8.57; N, 4.41.

EXAMPLE 3 trans-6-(i-Propyl)-2,2-dimethyl-4-(2-oxo-pyrrolidinyl)-2H-1-benzopyran-3-ol (E3)

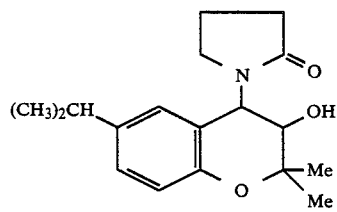

Trans-6-(i-propyl)-3,4-epoxy-3,4-dihydro-2,2-dimethyl-2H-1-benzopyran (1.89 g) reacted as in Example 2 to give the title compound (0.31 g) as fine white needles having M.pt. 167°–173° C.

$^1$H nmr (CDCl$_3$)

1.19 (d, J=7 Hz, 6H)
1.26 (s, 3H)
1.49 (s, 3H)
2.10 (m, 2H)
2.58 (m, 2H)
2.80 (septet, J=7 Hz, 1H)
2.95 (d, J=6 Hz, 1H)
3.10 (m, 1H)
3.25 (m, 1H)
3.75 (dd, J=10,6 Hz, 1H)
5.28 (d, J=10 Hz, 1H)
6.75 (m, 2H)
7.04 (dd, J=9,3 Hz, 1H).

Mass spectrum: Found M$^+$ 303.1843; C$_{18}$H$_{25}$NO$_3$ requires 303.1835.

Analysis: Found C, 71.43, 71.12; H, 8.54, 8.43; N, 4.59, 4.58; C$_{18}$H$_{25}$NO$_3$ requires C, 71.26; H, 8.31; N, 4.62.

EXAMPLE 4 trans-3,4-Dihydro-2,2,6-trimethyl-4-(2-oxopyrrolidinyl)-2H-1-benzopyran-3-ol (E4)

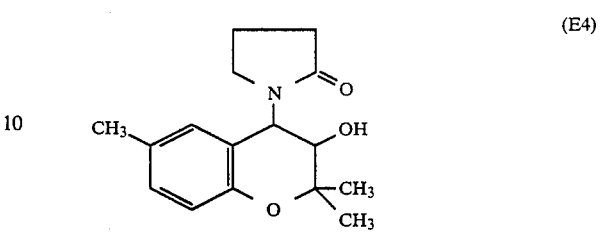

2-Pyrrolidone (1.02 g) was added to a suspension of sodium hydride (0.3 g, 80% dispersion in oil) in dry dimethyl sulphoxide (20 ml) under nitrogen at room temperature, and the mixture stirred for 1 h. A solution of 3,4-epoxy-3,4-dihydro-2,2,6-trimethyl-2H-1-benzopyran in dry dimethyl sulphoxide (10 ml) was then added, and the reaction mixture stirred for an additional 16 h. Cautious addition of water and extraction via ethyl acetate gave a crude product (1.84 g) which was chromatographed on silica gel and eluted with 60°–80° C. petroleum ether-ethyl acetate mixtures to give a foam (0.7 g) which was recrystallised from 60°–80° C. petroleum ether-ethyl acetate (0.53 g). Two further recrystallizations from ethyl acetate-pentane gave the analytical sample of the title compound mp 187°–188° C.

Analysis: Found C, 70.01; H, 8.10; N, 4.83. C$_{16}$H$_{21}$NO$_3$ requires C, 69.79; H, 7.69; N, 5.09.

EXAMPLE 5 trans-3,4-Dihydro-2,2,6-trimethyl-4-[N,N-dimethyl-2-acetamido]-2H-1-benzopyran (E5)

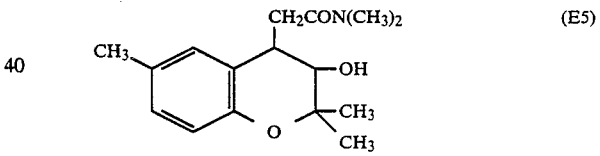

A solution of lithium diisopropylamine in tetrahydrofuran (20 ml) was prepared at −20° from n-butyl lithium (6.7 ml, 1.5M soln. in hexane) and diisopropylamine (1.4 ml) under N$_2$. A solution of N,N-dimethylacetamide (0.87 g) in tetrahydrofuran (15 ml) was then added dropwise at −20° C. and the solution stirred for 0.5 h. A solution of 3,4-epoxy-3,4-dihydro-2,2,6-trimethyl-2H-1-benzopyran (1.9 g) in tetrahydrofuran (20 ml) was then added at 0° C. and the mixture allowed to attain room temperature and then refluxed for 2 h. After cooling, the reaction mixture was partitioned between ethyl acetate and dil. HCl, and the organic layer washed with water, brine and then dried over anhydrous MgSO$_4$, filtered and evaporated, to give a white solid which was recrystallized from ethyl acetate-60°–80° C. petroleum ether (0.26 g) as an off-white solid m.p. 151°–153° C.

NMR (CDCl$_3$) δ

1.15 (s, 3H)
1.47 (s, 3H)
2.27 (s, 3H)
2.63 (q, J=17,10 Hz, 1H)
3.04 (s, 3H)
3.08 (s, 3H)
3.15 (q, J=17,2 Hz, 1H)

3.27 (t, J=10,9 Hz, 1H)
3.53 (q, J=9,3 Hz, 1H, collapsing to J=9 Hz on addition of D₂O)
5.33 (d, J=3 Hz, 1H exchangeable with D₂O)
6.73 (d, J=8 Hz, 1H)
6.93 (m, 2H).

EXAMPLE 6 trans-4-Acetylamino-3,4-dihydro-2,2,6-trimethyl-2H-1-benzopyran-3-ol (E6)

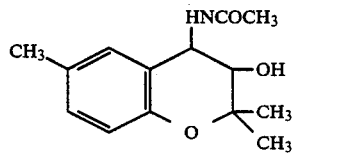

(E6)

To the crude aminoalcohol of description 7 (1.0 g) in dichloromethane (60 ml) and triethylamine (0.47 ml) was added acetyl chloride (0.34 ml) dropwise, with stirring at room temperature. After the reaction mixture had been stirred for an additional 3 h the organic phase was washed with water and brine before drying over anhydrous MgSO₄. Filtration and evaporation and chromatography (chromatotron 30% pentane-EtOAc-EtOAc) and recrystallization from EtOAc gave the title compound m.p. 188°–190° C.

EXAMPLE 7 trans-3,4-Dihydro-2,2,6-trimethyl-2-(N-methylureido)-2H-1-benzopyran-3-ol (E7)

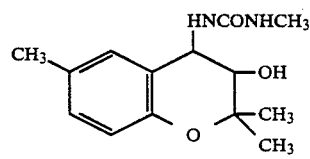

(E7)

To the crude aminoalcohol of description 7 (1 g) dissolved in dichloromethane (40 ml) was added methyl isocyanate (0.46 ml) during 5 min with stirring at 0° C. After an additional 2 h at 0° C., the solution was washed with water and brine and dried over anhydrous MgSO₄. Filtration and evaporation and chromatography (chromatotron CHCl₃-10% MeOH-CHCl₃) gave a solid which was recrystallised from ethyl acetate-60°–80° C. petroleum ether (450 mg). A further recrystallistion of a small amount gave the title compound as the 0.25 hydrate, m.p. 170°–171° C.

NMR (CDCl₃) δ
1.22 (s, 3H)
1.43 (s, 3H)
2.25 (s, 3H)
2.79 (s, 3H)
3.51 (d, J=9 Hz, 1H)
4.74 (d, J=9 Hz, 1H)
6.63 (d, J=8 Hz, 1H)
6.93 (q, J=8,2 Hz, 1H)
7.03 (narrow m, 1H).

EXAMPLE 8 trans-4-(4-Fluorobenzoylamino)-3,4-dihydro-2,2-dimethyl-6-isopropyl-2H-1-benzopyran-3-ol (E8)

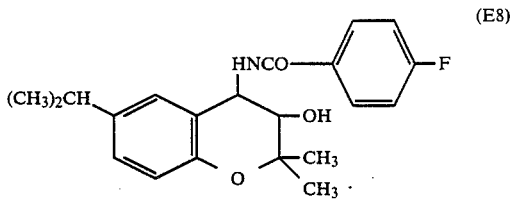

(E8)

To the aminoalcohol of description 8 (1.45 g), and triethylamine (0.94 ml) in dichloromethane (50 ml) cooled to 0° C. under nitrogen, was added p-fluorobenzoyl chloride (0.8 ml). The mixture was stirred for a further 10 min at 0° C. and for 16 h at room temperature, and then washed with water containing a little sodium hydroxide solution, and brine. The organic layer was dried over anhydrous magnesium sulphate, filtered and evaporated and the crude solid recrystallised from ethyl acetate-60°–80° C. petroleum ether to give the compound of this example as a white solid (0.66 g) of mp 235°–236° C.

Mass spectrum M⁺ at m/z 357.1740.
C₂₁H₂₄NO₃F requires 357.1750.

EXAMPLE 9 trans-3,4-Dihydro-6-hydroxymethyl-2,2-dimethyl-4-(2-oxopyrrolidinyl)-2H-1-benzopyran-3-ol (E9)

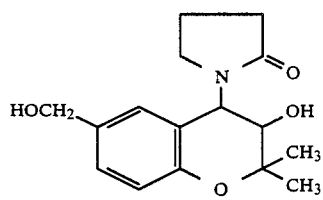

(E9)

To trans-6-Formyl-3,4-dihydro-2,2-dimethyl-4-(2-oxopyrrolidinyl)-2H-1-benzopyran (0.5 g, described in J. Med. Chem. 29, 2194 (1986)) dissolved in ethanol (10 ml) and methanol (10 ml) cooled in an ice bath was added sodium borohydride (65 mgm) under nitrogen, and the mixture stirred for 1.5 h. The solution was acidified to pH 3 with glacial acetic acid, and diluted with water (200 ml) and extracted with methylene chloride. The organic layer was washed with brine and dried over anhydrous magnesium sulphate. Filtration and evaporation gave a foam (0.41 g) which was recrystallised twice from ethyl acetate-60°–80° C. petroleum ether to give the compound of this example of mp 175°–178° C.

Mass spectrum (EI) M⁺ at m/z 291.1471.
C₁₆H₂₁O₄N requires 291.1471.

EXAMPLE 10 trans-6-Aminomethyl-3,4-dihydro-2,2-dimethyl-4-(2-oxopyrrolidinyl)-2H-1-benzopyran-3-ol (E10)

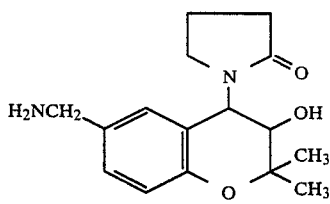
(E10)

trans-6-Cyano-3,4-dihydro-2,2-dimethyl-4-(2-oxopyrrolidinyl)-2H-1-benzopyran-3-ol (5 g, prepared as described in *J. Med. Chem.* 29, 2194 (1986)), in ethanol (375 ml) and glacial acetic acid (75 ml) containing concentrated HCl (5 ml) was shaken in the presence of 10% Pd/C (1 g) in an atmosphere of hydrogen for 4 h. The catalyst was filtered off and the solution neutralised with 10% aqueous NaOH solution, and the solution evaporated to dryness. Acid-base extraction, and drying of a dichloromethane solution of the residue, furnished, after recrystallisation from ethyl acetate-pentane, 2.03 g of the required aminomethyl compound of example 4 of mp 191°–193° C. as the hemihydrate.

NMR (CD$_3$)$_2$SO δ
1.14 (s, 3H)
1.41 (s, 3H)
1.95 (m, 2H)
2.39 (m, 2H)
2.88 (m, 1H)
3.28 (m, 3H including 2H exchangeable with D$_2$O)
3.58 (s, 2H)
3.64 (d, J=10 Hz, 1H)
4.97 (d, J=10H, 1H)
5.53 (m, 1H exchangeable with D$_2$O)
6.70 (d, J=8 Hz, 1H)
6.81 (narrow m, 1H)
7.09 (q, J=8,2 Hz, 1H).

EXAMPLE 11 trans-6-Acetylaminomethyl-3,4-dihydro-2,2-dimethyl-4-(2-oxopyrrolidinyl)-2H-1-benzopyran-3-ol (E11)

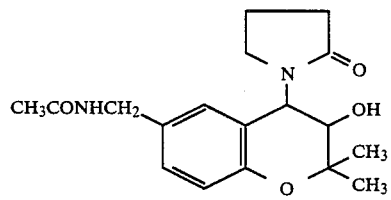
(E11)

To the compound of example 10 (0.57 g) and triethylamine (0.55 ml) stirred in dichloromethane (50 ml) was added acetyl chloride (0.154 ml) dropwise, at 0° C. After 2 h at 0° C., more acetyl chloride (0.154 ml) was added and the reaction mixture stirred for a further 16 h and allowed to attain room temperature. The organic phase was washed with water and brine and dried over anhydrous magnesium sulphate. Filtration and evaporation gave the crude product (0.33 g) which was recrystallised from ethyl acetate-dichloromethane to give the title compound (0.24 g) as colourless crystals of mp 206°–208° C.

Mass spectrum (EI) M+ at m/z 332.1735.
Calcd. for C$_{18}$H$_{24}$N$_2$O$_4$ 332.1745.

EXAMPLE 12 trans-6-(N,N-dimethylaminomethyl)-2,2-dimethyl-4-(2-oxopyrrolidinyl)-2H-benzopyran-3-ol (E12)

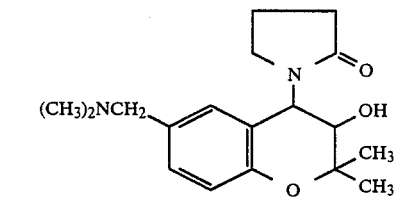
(E12)

A solution of trans-6-(aminomethyl)-2,2-dimethyl-4-(2-oxopyrrolidinyl)-2H-benzopyran-3-ol (0.828 g, example 10) and aqueous formaldehyde solution (37/40% w/v) (3 ml) in methanol (10 ml) was heated under reflux, with stirring, for 30 min. After cooling to ice-bath temperature, sodium borohydride (0.4 g) was added portionwise. After stirring for 1 h at room temperature, the reaction mixture was evaporated in vacuo to give a cloudy oil. Water was added, and the mixture extracted into chloroform. The organic extracts were washed with brine and dried over anhydrous sodium sulphate, and the solvent evaporated in vacuo to give an oil. Column chromatography (Kieselgel 60, eluting with chloroform-methanol) gave a colourless oil (0.5 g). The oil was dissolved in the minimum ethyl acetate and allowed to stand overnight. The crystals which formed were filtered off and recrystallised from ethyl acetate to give the title compound as fine white needles (0.25 g) having m.p. 156°–7° C.

$^1$H nmr (CDCl$_3$) δ
1.26 (s, 3H)
1.49 (s, 3H)
1.94–2.16 (m, 2H)
2.23 (s, 6H)
2.50–2.63 (m, 2H)
3.01 (br.s, 1H)
3.06–3.17 (m, 1H)
3.18–3.32 (m, 1H)
3.37 (s, 2H)
3.75 (d, J=10 Hz, 1H)
5.28 (d, J=10 Hz, 1H)
6.79 (d, J=8 Hz, 1H)
6.86 (d, J=2 Hz, 1H)
7.12 (d.d., J=8, 2 Hz, 1H).

Mass spectrum: Found M+ 318.1955;
C$_{18}$H$_{26}$N$_2$O$_3$ requires 318.1944.

Analysis: Found C, 67.73; H, 8.09; N, 8.59.
C$_{18}$H$_{26}$N$_2$O$_3$ requires C, 67.90; H, 8.23; N, 8.80.

EXAMPLE 13 trans-6-Ethyl-3,4-dihydro-2,2-dimethyl-4-(2-oxopyrrolidinyl)-2H-1-benzopyran-3-ol (E13)

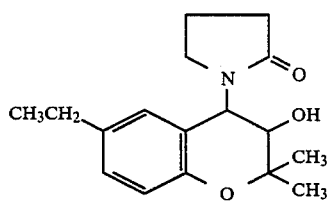
(E13)

To a mixture of pyrrolidone (0.416 g) and sodium hydride (0.146 g, 80% dispersion in oil) in dimethyl sulphoxide (50 ml was added the epoxide of description 11 (1.0 g). The mixture was stirred at room temperature under nitrogen for 4 h. Cautious addition of water and extraction via ethyl acetate gave an oil which was purified on the chromatotron (20% ethyl acetate-60°–80° C. petroleum ether-ethyl acetate) to give the compound of example 13 after recrystallisation from ethyl acetate-60°–80° C. petroleum ether as crystals of mp 154°–163° C.

Mass spectrum (EI) M+ at m/z 289.1683.
$C_{17}H_{23}NO_3$ requires 289.1678.

EXAMPLE 14 trans-3,4-Dihydro-2,2-dimethyl-4-(2-oxopyrrolidinyl)-6-cyclopentyl-2H-1-benzopyran-3-ol (E14)

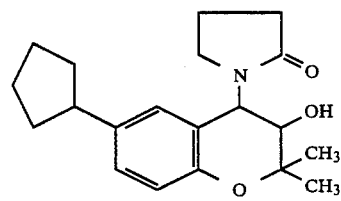
(E14)

To the epoxide of description 14 (1.5 g) dissolved in dimethyl sulphoxide (15 ml) was added pyrrolidone (0.404 g) with stirring under nitrogen. Sodium hydride (0.142 g, 80% dispersion in oil) was added to the mixture which was stirred for 18 h. Cautious addition of water and extraction via ethyl acetate gave the title compound (0.55 g) after recrystallisation from ethyl acetate-pentane m.p. 179°–184° C.

Mass spectrum (EI) M+ at m/z 329.1993.
$C_{20}H_{27}NO_3$ requires 329.1991.

EXAMPLE 15 trans-2,2-Dimethyl-6-(1,3-dioxo-2-isoindoline)methyl-4-(2-oxopyrrolinyl)-2H-1-benzopyran-3-ol

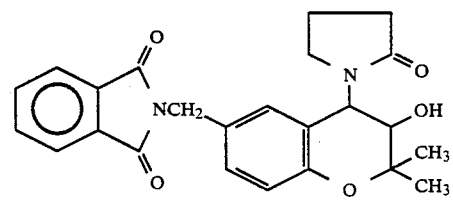
(E15)

A mixture of trans-6-(aminomethyl)-2,2-dimethyl-4-(2-oxopyrrolidinyl)-2H-1-benzopyran-3-ol (0.68 g example 10), N-carboethoxy-phthalimide (0.62 g) and sodium bicarbonate (0.414 g) in water (5 ml) was stirred for 17 h at room temperature. The white solid was removed by filtration, washed with water and dried in vacuo. Recrystallisation from chloroform/ethyl acetate gave the title compound as a white solid (0.74 g), having m.p. 220°–221.5° C.

$^1$H-nmr (CDCl$_3$) δ
1.24 (s, 3H)
1.47 (s, 3H)
2.01–2.18 (m, 2H)
2.47–2.70 (m, 2H)
3.01–3.13 (m, 1H)
3.13–3.26 (m, 2H)
3.7 (dd J=10, 4 Hz, 1H)
4.66 (d, J=14 Hz, 1H)
4.81 (d, J=14 Hz, 1H)
5.26 (d, J=10 Hz, 1H)
6.76 (d, J=8 Hz, 1H)
7.03 (d, J=2 Hz, 1H)
7.24 (dd, J=8, 2 Hz, 1H)
7.66–7.75 (m, 2H)
7.78–7.88 (m, 2H)

Mass spectrum: Found M+ 420.1682.
$C_{24}H_{24}N_2O_5$ requires 420.1685.
Analysis: Found C, 68.45; H, 5.75; N, 6.57.
$C_{24}H_{24}N_2O_5$ requires C, 68.56; H, 5.75; N, 6.66.

EXAMPLE 16

4-Chloroacetamido-3,4-dihydro-2,2,6-trimethyl-2H-1-benzopyran (E16)

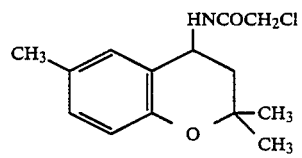
(E16)

To a solution of 4-amino-3,4-dihydro-2,2,6-dimethyl-2H-1-benzopyran (1.63 g, described in Khim. Geterot. Soed. 5 (3), 434, 1969) in 40 ml dichloromethane at 0° C. was added triethylamine (1.2 ml) followed by chloroacetyl chloride (0.96 g). The solution was stirred for 16 h then washed with saturated brine solution, separated, dried (MgSO$_4$) and concentrated to a cream solid. Chromatography (silica, CH$_2$Cl$_2$ eluent) provided 4-chloroacetamido-3,4-dihydro-2,2,6-trimethyl-2H-1-benzopyran (1.78 g, 78%) as a white solid. m.p. 147°–148° C.

NMR (CDCl$_3$) δ
1.3 (s, 3H)
1.4 (s, 3H)
1.75 (d.d., J=13.2, 10.7 Hz, 1H)
2.25 (d.d., J=13.2, 6.6 Hz, 1H)
2.3 (s, 3H)
4.15 (ABq, J=15.6 Hz, 2H)
5.25 (d.d., J=10.7, 6.6 Hz, 1H)
6.8 (br d, J=8 Hz, 1H)
7.0 (m, 2H).

PHARMACOLOGICAL DATA

Antihypertensive Activity

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5±0.5° C.) before transfer to a restraining cage. Each determination of blood pressure was the mean of at least 6 readings. Spontaneously hypertensive rats (ages 12-18 weeks) with systolic blood pressures >180 mmHg were considered hypertensive.

The compound of Example 1 gave a maximum fall in blood pressure of 33±2% at a dose of 1.0 mg/kg po.

The compound of Example 13 gave a maximum fall in blood pressure of 54±2% at a dose of 1.0 mg/kg po. Other compounds of the Examples, such as E2, E3 and E14 showed significant falls in blood pressure at a dose of 1.0 mg/kg po.

We claim:

1. A compound of formula (I) or, when the compound of formula (I) contains a salifiable group, a pharmaceutically acceptable salt thereof:

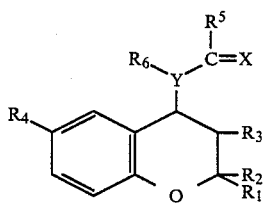

wherein:

Y is N;

one of $R_1$ and $R_2$ is hydrogen or $C_{1-4}$ alkyl and the other is $C_{1-4}$ alkyl or $R_1$ and $R_2$ together are $C_{2-5}$-polymethylene;

$R_3$ is hydrogen, hydroxy, $C_{1-6}$ alkoxy or $C_{1-7}$ unsubstituted carboxylic acyloxy;

$R_4$ is a $C_{3-8}$ cycloalkyl group, a $C_{1-6}$ alkyl group or a $C_{1-6}$ alkyl group substituted by amino;

$R_5$ and $R_6$ together are $-CH_2-(CH_2)_n-Z-(CH_2)_m-$ wherein m and n are 0 to 2 such that m+n is 1 or 2 and Z is $CH_2$;

X is oxygen or sulphur; and the nitrogen-containing group in the 4-position being trans to the $R_3$ group when $R_3$ is hydroxy, $C_{1-6}$ alkoxy or $C_{1-7}$ acyloxy.

2. A compound according to claim 1 wherein $R_1$ and $R_2$ are both methyl.

3. A compound according to claim 1 wherein $R_3$ is hydroxy.

4. A compound according to claim 1 where $R_4$ is $C_{5-7}$ cycloalkyl, $C_{1-4}$ alkyl or $C_{1-4}$ alkyl substituted by amino.

5. A compound according to claim 4 wherein $R_4$ is $C_{5-7}$ cycloalkyl or $C_{1-4}$ alkyl.

6. A compound according to claim 1 wherein X is oxygen.

7. A compound selected from the group consisting of trans-6-methyl-2,2-dimethyl-4-(2-oxopiperidinyl)-2H-1-benzopyran-3-ol, trans-6-t-butyl-2,2-dimethyl-4-(2-oxopyrrolidinyl)-2H-1-benzopyran-3-ol, trans-6-(i-propyl)-2,2-dimethyl-4-(2-oxopyrrolidinyl)-2H-1-benzopyran-3-ol, trans-3,4-dihydro-2,2,6-trimethyl-4-(2-oxopyrrolidinyl)-2H-1-benzopyran-3-ol, trans-6-aminomethyl-3,4-dihydro-2,2-dimethyl-4-(2-oxopyrrolidinyl)-2H-1-benzopyran-3-ol, trans-6-(N,N-dimethylaminomethyl)-2,2-dimethyl-4-(2-oxopyrrolidinyl)-2H-benzopyran-3-ol, trans-6-ethyl-3,4-dihydro-2,2-dimethyl-4-(2-oxopyrrolidinyl)-2H-1-benzopyran-3-ol, and trans-3,4-dihydro-2,2-dimethyl-4-(2-oxopyrrolidinyl)-6-cyclopentyl-2H-1-benzopyran-3-ol.

8. An antihypertensive pharmaceutical composition comprising an anti hypertensive effective amount of a compound according to claim 1 and a pharmaceutically acceptable carrier.

9. A method of treatment of hypertension in mammals which comprises the administration to the mammal in need of such treatment, an antihypertensive effective amount of a compound according to claim 1.

* * * * *